Figure 1:
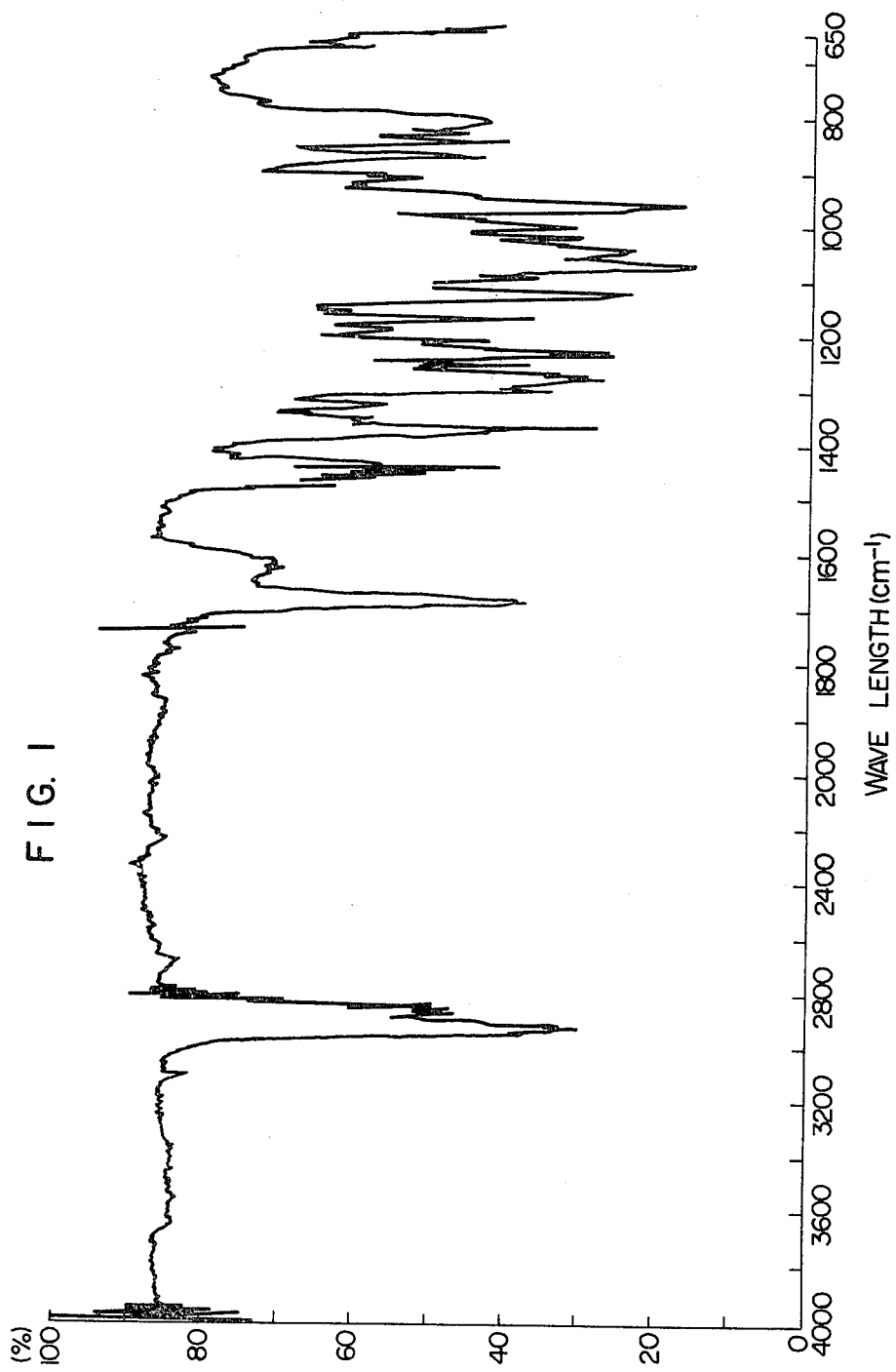

United States Patent [19]

Endo et al.

[11] 4,332,731

[45] Jun. 1, 1982

[54] 2-METHYLENE-1,4,6-TRIOXASPIRO[4,6]UNDECANE, PROCESS FOR THE PREPARATION THEREOF AND PROCESS FOR THE PREPARATION OF POLYMERS

[75] Inventors: Takeshi Endo, Yokohama; Takahisa Ogasawara, Tokai; Kiyokazu Mizutani, Inasawa, all of Japan

[73] Assignee: Toagosei Chemical Industry Co., Ltd., Tokyo, Japan

[21] Appl. No.: 188,267

[22] Filed: Sep. 17, 1980

[30] Foreign Application Priority Data

Sep. 22, 1979 [JP] Japan .................................. 54-121584

[51] Int. Cl.³ .......................................... C07D 317/02

[52] U.S. Cl. ................................ 549/334; 204/159.22; 204/159.24; 526/270

[58] Field of Search .................................. 260/340.9 R

[56] References Cited

PUBLICATIONS

Chem. Abstracts, Subject Index 1967–1971, p. 31986s.

*Primary Examiner*—Ethel G. Love
*Attorney, Agent, or Firm*—Cooper, Dunham, Clark, Griffin & Moran

[57] ABSTRACT

Novel 2-methylene-1,4,6-trioxaspiro[4,6]undecane has both cationic polymerizability and radical ring-opening polymerizability, and it can be produced by reacting a 2-halomethyl-1,4,6-trioxaspiro[4,6]undecane with an alkali to effect dehydrohalogenation.

1 Claim, 3 Drawing Figures

2-METHYLENE-1,4,6-TRIOXASPIRO[4,6]UNDECANE, PROCESS FOR THE PREPARATION THEREOF AND PROCESS FOR THE PREPARATION OF POLYMERS

This invention relates to 2-methylene-1,4,6-trioxaspiro[4,6]undecane [hereinafter referred to as compound (1)] which is a novel compound and useful as a polymerizable monomer, and this compound is represented by the formula (1):

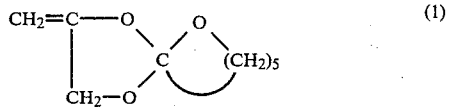   (1)

The compound (1) can be prepared dehydrohalogenation of 2-halomethyl-1,4,6-trioxaspiro[4,6]undecane [hereinafter referred to as compound (2)] represented by the formula (2):

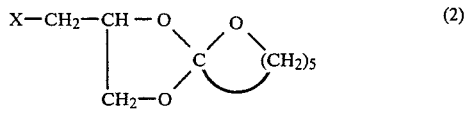   (2)

wherein X is a halogen atom such as Cl, Br or I.

This reaction can be depicted by the following formulas:

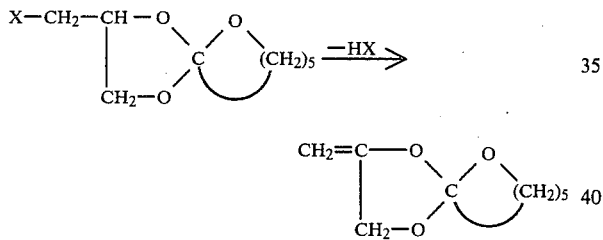

The compound (2) is already known (Japanese Patent Publication Nos. 28111/69 and 7949/69), but dehydrohalogenation of this compound as effected by reacting it with an alkali such as sodium alkoxide in a suitable solvent such as dimethylformamide and pyridine results in the novel compound (1). The reaction proceeds at room temperature, but, if necessary, the reaction temperature may be further lowered or raised. The degree of progress of the reaction can be easily detected by analyzing the reaction solution by, for example, a liquid chromatography.

Separation and withdrawal of the compound (1) from the reaction mixture can be attained by, for example, pouring the reaction mixture into water to separate the organic layer and the aqueous layer, extracting the aqueous layer with an organic solvent such as diethyl ether, chloroform, benzene, etc., joining the extract layer and said organic layer, dehydrating the combined layer, distilling off the solvent and further distilling the residue under reduced pressure.

Cationic polymerization of the spiro-orthoesters to which the compound (1) of this invention belongs is mentioned in, for example, the Journal of Macromolecular Science, Chemistry, A9(5), 849–865 (1975), and the like, but the present inventors have unveiled a surprising fact that the compound (1) is capable of not only cationic polymerization but also radical ring-opening polymerization.

No light has ever been shed on radical polymerizability of spiro-orthoesters. As regards the spiro-orthocarbonates having some analogy to the spiro-orthoesters in chemical structure, their radical ring-opening polymerizability has been discussed in, for example, Journal of Polymer Science, Polymer Chemistry Edition, 13, 2,525–2,530 (1975) or the like but the synthesis of such spiro-orthocarbonates is complicated and also necessitates use of harmful, low-boiling $CS_2$ or other expensive materials, so that it is not easy to produce such compounds and also the objective product tends to become costly.

The compound (1) of this invention, however, can be easily synthesized by a simple reaction—dehydrohalogenation—using as the starting material the compound (2) which can be synthesized from a commercially available inexpensive epihalohydrin and $\epsilon$-caprolactone.

Further, the compound (1) has the characteristic feature that the volumetric shrinkage at the time of polymerization is very little. It is considered that the polymerization of the compound (1) progresses with the following reaction mechanism:

Radical polymerization mechanism:

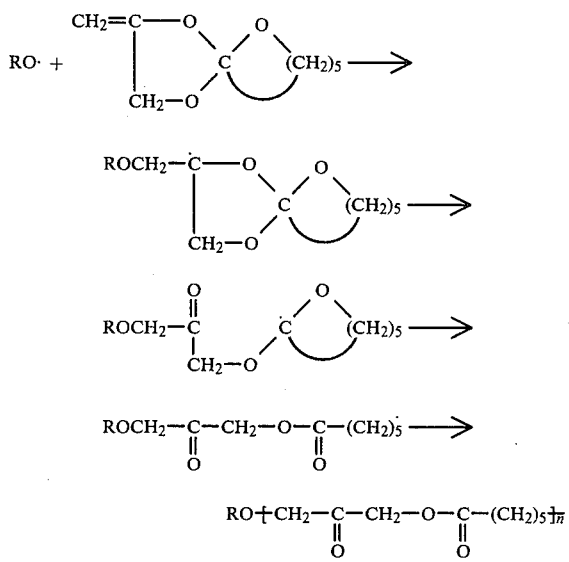

Cationic polymerization mechanism:

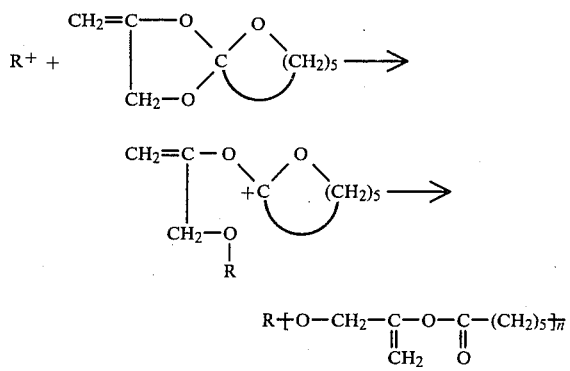

The compound (1) undergoes radical polymerization in the presence of a radical polymerization initiator, and during this polymerization reaction, as shown by the above reaction formulae, the double bonds of methylene groups disappear while there takes place the opening of the spiroester ring to give rise to an ester linkage, resulting in a viscous polymer.

The conventional radical polymerizable monomers or cationic polymerizable monomers suffer a very great volumetric shrinkage during polymerization as shown in Table 1.

TABLE 1

| | Volumetric shrinkage of conventional monomers during polymerization | |
|---|---|---|
| | Monomer | Volumetric shrinkage during polymerization (%) |
| Radical polymerization | Ethylene | 66.0 |
| | Vinyl chloride | 34.4 |
| | Acrylonitrile | 31.0 |
| | Vinyl acetate | 20.9 |
| | Styrene | 14.5 |
| | Methyl methacrylate | 21.2 |
| | Ethyl methacrylate | 17.8 |
| Cationic polymerization | Ethylene oxide | 23 |
| | Propylene oxide | 17 |
| | Styrene oxide | 9 |
| | Epichlorohydrin | 12 |

A great volumetric shrinkage during polymerization gives rise to various problems such as unsatisfactory dimensional precision in use of the polymer as molding material, straining an insert when using the polymer as casting material, lowering the adhesion to the mold, formation of voids, and so forth. Also, in case of using the polymer as a coating material, there occurs warping or lowering of adhesion to the coated base due to internal strain, and in use as an adhesive, there take place drop of adhesion, warping, deformation, etc., owing to internal strain.

In the case of the compound (1), the volumetric shrinkage that occurs when polymerizing this compound with a radical polymerization catalyst is approximately 6.0% and the volumetric shrinkage which occurs in cationic polymerization is approximately 5.5%. Thus, the volumetric shrinkage suffered by the compound (1) during its polymerization is very little as compared with the conventional radical-polymerizable vinyl monomers and cationic-polymerizable monomers.

The "volumetric shrinkage" (%) as referred to herein is represented by: [1 − (specific gravity of the compound (1)/specific gravity of the polymer)] × 100.

As viewed above, the compound (1) of this invention can be produced with ease and at low cost and can be also polymerized by either radical polymerization or cationic polymerization, and further the volumetric shrinkage suffered by the compound during its polymerization is minimized.

Thus, the compound (1) of this invention is very useful one that can be favorably used as molding material, composite material, adhesive, casting material, coating material and so forth.

An explanation is made below of the polymerization means for the compound (1) according to this invention.

As mentioned above, the compound (1) of this invention can be polymerized by radical or cationic mechanism. The polymerization is initiated by irradiation of ultraviolet rays; supplying heat energies from heat oven, infrared rays or microwaves; and irradiation of high energy ionizing radiation such as electron beam or X-rays. In the case of heat energy or ultraviolet polymerization, a heat polymerization initiator (radical or cationic) or photo-initiator (radical or cationic) is used to polymerize the compound (1) of this invention. Polymerization by means of ionizing radiation such as electron beam or X-rays, is usually carried out in a non-catalytic system.

In the case of ultraviolet radical polymerization, usually a radical photo-initiator is used. Among the radical photo-initiators favorably usable for this purpose are, for example, carbonyl compounds such as acetophenone, 2,2-dimethoxy-2-phenylacetophenone, 2,2-diethoxyacetophenone, 4'-isopropyl-2-hydroxy-2-methyl-propiophenone, 2'-hydroxy-2-methyl-propiophenone, 4,4'-bis-diethylaminobenzophenone, benzophenone, methyl-(o-benzoyl)-benzoate, 1-phenyl-1,2-propanedion-2-(o-ethoxycarbonyl)-oxim, or 1-phenyl-1,2-propanedion-2-(o-benzoyl)-oxim; benzoin; benzoin derivatives such as benzoin methyl ether, benzoin ethyl ether, benzoin isopropyl ether, benzoin isobutyl ether, or benzoin octyl ether; benzil; diacetyl; anthraquinone, xanthon or their derivatives such as methylanthraquinon, chloroanthraquinone, chlorothioxanthone, 2-methylthioxanthone or 2-i-propylthioxanthone; sulfur compounds such as diphenyl sulfide or diphenyl disulfide; dithiocarbamate; α-chloromethylnaphthalene; and anthracene. These initiators may be used alone or in combination. In the case of radical polymerization by heat energy such as infrared rays, heat or microwaves, it is possible to use any known type of radical heat polymerization initiator provided that it is capable of producing a radical by decomposition due to heat energy. For instance, there may be used an organic peroxide such as di-tert-butyl peroxide, 2,5-dimethyl-2,5-di(tertbutyl-peroxide)hexane, tert-butyl hydroperoxide or tert-butyl peroxybenzoate; an azo compound such as azoisobutylonitrile; and inorganic peroxide such as ammonium persulfate or potassium persulfate; and the like. These initiators may be used alone or in combination.

As examples of the cationic photo-initiator usable for ultraviolet cationic polymerization, there may be cited aromatic diazonium salts such as

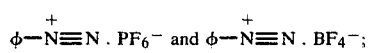

aromatic halonium salts such as $\phi-I^+-\phi\cdot BF_4^-$; aromatic onium salts of the Group Va elements of the Periodic Table such as

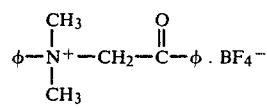

and aromatic onium salts of the Group VIa elements of the Periodic Table such as

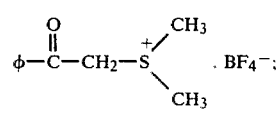

carbonyl chelates of the Group IIIa–Va element of the Periodic Table such as

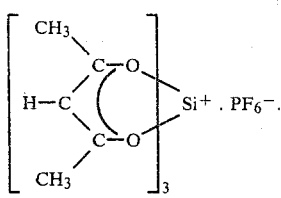

These initiators may be used alone or in combination.

As the heat polymerization initiator usable for other modes of cationic polymerization by heat energy such as infrared rays, heat or microwaves, there may be mentioned Lewis acids such as $BF_3$, $FeCl_3$, $SnCl_4$, $SbCl_5$, $SbF_3$, $TiCl_4$, etc.; coordination compounds of Lewis acids with compounds having O, S or N such as $BF_3OEt_2$, $BF_3$-aniline complexes, etc.; oxonium salts, diazonium salts and carbonium salts of Lewis acids; halides, mixed halides; and perhalogeno-acid derivatives. These initiators may be used alone or in combination.

In case of using a photo-initiator or a heat polymerization initiator, the amount of such initiator used is suitably selected from the range of 0.01 to 10% by weight, preferably 0.1 to 5% by weight, based on the weight of the monomer, depending on the purpose of use.

In case the polymerization is carried out under irradiation of ultraviolet rays or ionizing radiation, the polymerization reaction advances at room temperature, but in other cases the reaction advances smoothly under heating or under heated conditions. The polymerization temperature is usually selected from the range of 30° to 200° C.

Figure 2:
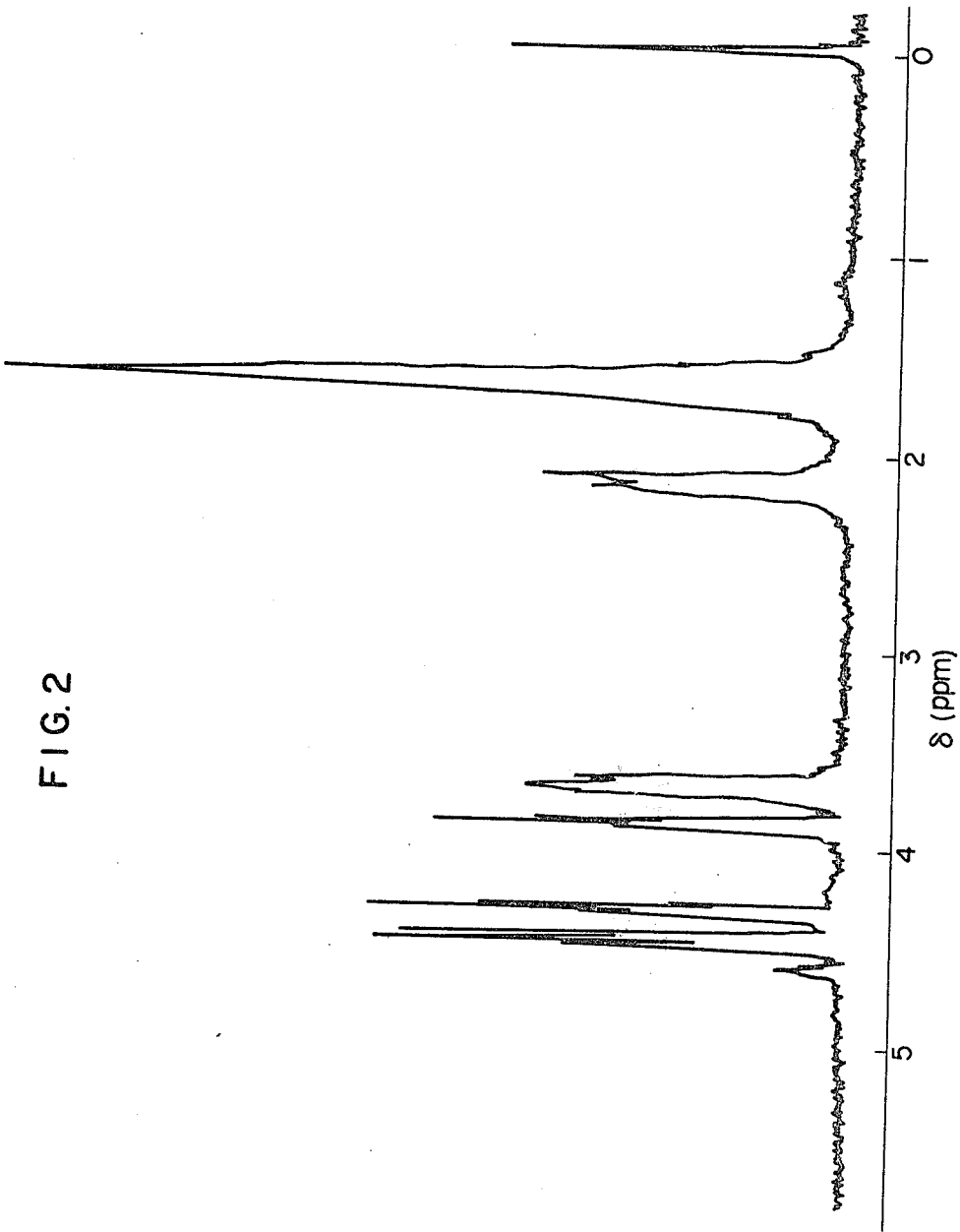
Figure 3:
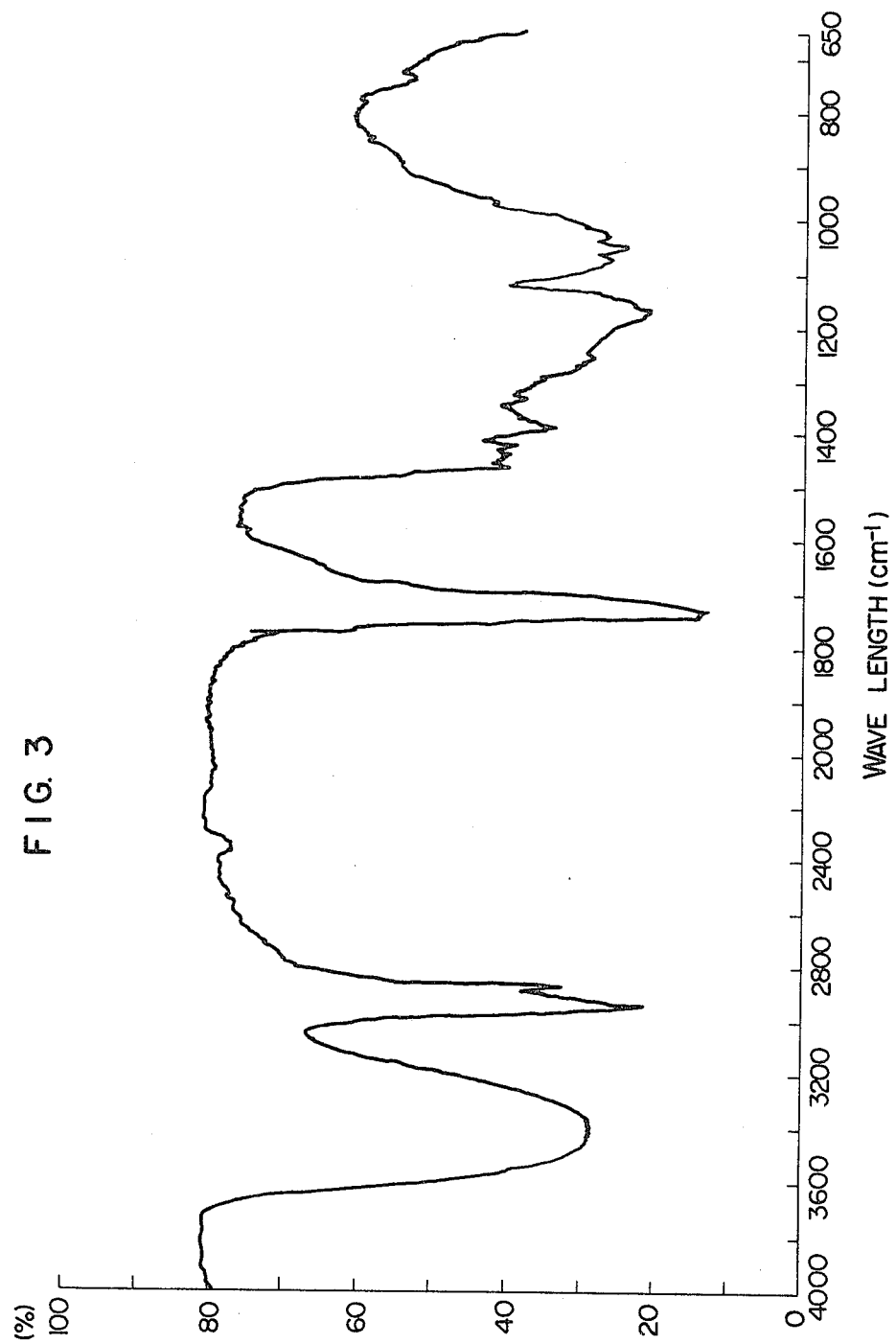

The invention is now described in further detail referring to Examples thereof while referring to the accompanying drawings. In the drawings, FIG. 1 is an infrared absorption spectral diagram of the compound (1); FIG. 2 is an NMR spectral diagram of the compound (1); and FIG. 3 is an infrared absorption spectral diagram of a polymer obtained by subjecting the compound (1) to a radical polymerization according to Example 2-(1).

EXAMPLE 1

43 g of sodium methoxide was mixed in 150 ml of dehydrated dimethylformamide, and after cooling the mixture to 10° C., 80.8 g of a compound of the formula (2) (wherein X is Cl) was added dropwise to said mixture under agitation over the period of about 90 minutes while passing nitrogen gas. Thereafter, stirring of the mixture was continued at room temperature for approximately 6 hours and then the reaction solution was poured into 1 liter of water to separate the aqueous layer and the organic layer.

Then the aqueous layer was extracted by adding 100 ml of diethyl ether, such extraction operation being repeated three times, and each ether layer was joined with said organic layer and dehydrated with magnesium sulfate, followed by evaporation of the ether.

The residue was further distilled under reduced pressure to obtain 50 g of the compound (1). The yield of the compound (1) was 75% and its property values were as shown below.

Elemental analysis (%): Calcd. for $C_9H_{14}O_3$ (theoretical): C, 63,5; H, 8.2. Found: C, 62.5; H, 8.1.

Specific gravity: 1.091/25° C. Boiling point: 87°–89° C./7 mmHg.

Infrared absorption spectrum: 960, 1070, 1120 cm$^{-1}$ (C—O—C), 1690 cm$^{-1}$ (C=C) (See FIG. 1).

NMR spectrum (in CDCl$_3$): δ(ppm): 4.5 (2H), 4.2 (2H), 3.9 (2H), 2.15 (2H), 1.65 (6H) (see FIG. 2).

The compound (2) used in this Example was prepared in the following way: 342 g (3 mol) of ε-caprolactone and 6 ml of $BF_3OEt_2$ were dissolved in 750 ml of methylene chloride and the mixed solution was cooled to about 10° C. in a nitrogen stream. To this solution maintained at 20°–25° C. was added dropwise a solution prepared by dissolving 333 g (3.6 mol) of epichlorohydrin in 350 ml of methylene chloride. After this dropwise addition, the mixed solution was further reacted at 25° C. for 5 hours and then 10 ml of triethylamine was added to deactivate the catalyst. Then the solution was washed three times with 1-liter portions of distilled water and dried overnight with magnesium sulfate. Then the solvent was removed and the residue was distilled under reduced pressure to obtain 378 g (61% yield) of the compound (2) (boiling point: 105°–107° C./2 mmHg).

EXAMPLE 2

The compound (1) was subjected to radical polymerization in the following way.

(1) To the compound (1) was added 3 mol% of di-tert-butyl peroxide as polymerization catalyst and the mixture was reacted in a sealed tube at 120° C. for 24 hours. The reaction product was dissolved in methylene chloride and the solution was poured into n-hexane to precipitate the polymer. There was obtained a yellow viscous polymer in a yield of approximately 50%.

The peaks at 1690 cm$^{-1}$, 1120 cm$^{-1}$ and 810 cm$^{-1}$ disappeared while the peaks appeared at 3480 cm$^{-1}$ and 1730–1740 cm$^{-1}$. The specific gravity of this polymer was 1.161 (at 25° C.) and the volumetric shrinkage during polymerization as calculated therefrom was 6.0%.

(2) To the compound (1) was added 5% by weight of benzoin ethyl ether, and the mixture was irradiated 20 times with ultraviolet rays by a 80 w/cm input ozone type condensing high pressure mercury lamp at a rate of 10 m/min.

Examination of the irradiated product by a liquid chromatography showed formation of a polymer.

EXAMPLE 3

The compound (1) was subjected to cationic polymerization in the following way:

To the compound (1) was added 0.5% by weight of $BF_3OEt_2$ as a polymerization catalyst and the mixture was polymerized at 30° C. for 20 hours. There was produced a brown viscous polymer.

This polymer had a specific gravity of 1.154 (at 25° C.) and the volumetric shrinkage during polymerization as calculated from said value was approximately 5.5%.

What is claimed is:
1. 2-Methylene-1,4,6-trioxaspiro[4,6]undecane.

* * * * *